United States Patent [19]
Konrad et al.

[11] Patent Number: 5,723,339
[45] Date of Patent: Mar. 3, 1998

[54] METHOD OF ANALYZING GOLD ELECTROPLATING SOLUTIONS FOR ARSENIC(III)

[75] Inventors: John Joseph Konrad, Endicott; Robert Anthony Sinicki, Endwell, both of N.Y.

[73] Assignee: International Business Machines Corporation, Armonk, N.Y.

[21] Appl. No.: 632,231

[22] Filed: Apr. 15, 1996

[51] Int. Cl.$^6$ ............................ G01N 33/20; G01N 21/74; G01N 1/00
[52] U.S. Cl. ................. 436/73; 436/80; 436/171; 436/175; 436/178
[58] Field of Search ....................... 436/73, 80, 103, 436/171, 175, 178

[56] References Cited

U.S. PATENT DOCUMENTS

| | | |
|---|---|---|
| 3,775,121 | 11/1973 | Sharp . |
| 4,071,427 | 1/1978 | Cheng et al. . |
| 4,365,969 | 12/1982 | Karpov et al. ........................ 436/75 |
| 5,318,687 | 6/1994 | Estes et al. ........................ 205/80 |
| 5,459,001 | 10/1995 | Estes et al. ........................ 430/5 |

FOREIGN PATENT DOCUMENTS 3-64482  3/1991  Japan .

OTHER PUBLICATIONS

S. Wakabayashi et al. *Kinzoku Hyoomen Gijutsu* 1987, 38, 223–227.
F.W.E Strelow et al. *Anal. Chem.* 1966, 38, 115–117.
H.A. Heller *Plating* 1969, 56, 277–284.
V.M. LeRoy et al. *Plating* 1973, 60, 922–927.
A.E. Smith *Analyst* 1975, 100, 300–306.
R. Belcher et al. *Analyst* 1975, 100, 522–523.
J. Aggett et al. *Analyst* 1976, 107, 341–347.
F.D. Pierce et al. *Anal. Chem* 1977, 49, 1417–1422.
M.M.M. El–Defrawy et al. *Anal. Chim. Acta* 1980, 115, 155–161.
C.J. Peacock et al. *Analyst* 1981, 106, 931–938.
J. J. Werbicki *Products Finishing* 1982, 42–53.
F. Puttemans et al. *Anal. Chim. Acta* 1982, 141, 225–232.
J.W. Hershey et al. *Spectrochim. Acta* 1986, 41B, 713–723.
S. Wakabayashi et al. *Chem. Abstr.* 1987, 107, 69885n.
X. Chi et al *Guangpuxue Yu Guangpu Fenxi* 1988, 8, 40–44.
E.M. Donaldson et al. *Talanta* 1988, 35, 297–300.
C. Boampong et al. *Anal. Chem.* 1988, 60 1185–1188.
F. Steglich *Chem. Abstr.* 1988, 108, 197484p.
R. R. Brooks et al. *Anal. Chim. Acta* 1989, 217, 165–170.
Y. An et al. *Spectrochim. Acta* 1992, 47B, 1403–1410.
M. Ochsenkuhn–Petropulu et al. *Can. J. Appl. Spectrosc.* 1995, 40, 61–5.
B. Jamoussi et al. *Fresenius J. Anal. Chem.* 1996, 356, 331–334.
"Reagent system increases atomic absorption sensitivity 20 to 100 times", Fishor Scientific Company, Jul. 1981.
"Determination Of Arsenic(III), Arsenic(V), Antimony(III), Antimony(V), Selenium(IV), and Selenium(VI) By Extraction With Ammonium Pyrrolidinedithiocarbamate–Methyl Isobutyl Ketone And Electrothermal Atomic Absorption Spectrometry", Analytica Chimica Acta, 124 (1981), pp. 131–142.
"Selective Determination Of Arsenic(III) And Arsenic(V) With Ammonium Pyrrolidinedithiocarbamate, Sodium Diethyldithiocarbamate and Dithizone By Means Of Flameless Atomic–Absorption Spectrophotometry With A Carbon––Tube Atomizer", Department of Chemistry, Hiroshima University, 1976, pp. 835–839.

*Primary Examiner*—Arlen Soderquist
*Attorney, Agent, or Firm*—Richard M. Goldman

[57] ABSTRACT

A method of analyzing for As(III) as $AsO_2^{-1}$ ion in an Au(I) containing electroplating solution. The concentration of As(III) in the electroplating solution is maintained high enough to avoid formation of "burnt Au" oxides but low enough to avoid bond failures. A sample of the electroplating solution is withdrawn and added to a buffered solution, for example an acetate-ethylene diamine tetraacetic acid (EDTA) buffered solution. A complexing agent for Au(I) ion is added to the buffered solution. This can be an alkali metal cyanide. Next ammonium pyrrolidine dithiocarbamate is added as a complexing agent for the $AsO_2^{-1}$ ion. The ammonium pyrrolidine dithiocarbamate—$AsO_2^{-1}$ ion is extracted, for example with methyl isobutyl ketone (MIBK). The extract is analyzed for As(III) by atomic absorption, as electrothermal atomic absorption spectrometry.

14 Claims, No Drawings

METHOD OF ANALYZING GOLD ELECTROPLATING SOLUTIONS FOR ARSENIC(III)

FIELD OF THE INVENTION

The invention relates to a method of analyzing for As(III) as $AsO_2^{-1}$ ion in an Au(I) containing electroplating solution. The concentration of As(III) in the electroplating solution is maintained high enough to maintain the limiting current density and avoid formation of "burnt Au" but low enough to avoid wire bond failures. A sample of the electroplating solution is withdrawn and added to a buffered solution, for example an acetate-ethylene diamine tetraacetic acid (EDTA) buffered solution. A complexing agent for Au(I) ion is added to the buffered solution. This can be an alkali metal cyanide. Next ammonium pyrrolidine dithiocarbamate is added as a complexing agent for the $AsO_2^{-1}$ ion. The ammonium pyrrolidine dithiocarbamate—$AsO_2^{-1}$ ion is extracted, for example with methyl isobutyl ketone (MIBK). The extract is analyzed for arsenic by electrothermal atomic absorption spectrometry.

BACKGROUND OF THE INVENTION

Gold is frequently used to provide contact surfaces for electrical contacts in electronic packages. This is because of gold's high electrical conductivity and its chemical resistance, i.e., its resistance to environmental attack. Gold contacts, pads, and lands are typically applied by electrodeposition from a plating solution, as an Au(I) containing plating solution. One such electroplating solution is a KAu(CN)$_2$ solution and other conductance salts.

Arsenic, as As(III) in the form of $AsO_2^{-1}$ ion, is present in the electroplating solution. The As is used as a "brightener." The concentration of As(III) in the electroplating solution is maintained high enough to maintain the limiting current density and avoid formation of "burnt Au" but low enough to avoid wire bond failures. The preferred range of As(III) in a KAu(CN)$_2$ solution, containing from about 3 to about 30 grams per liter KAu(CN)$_2$ is about 1 to about 10 milligrams per liter.

One problem encountered in the control of electroplating is the maintenance of the As(III) within this range. There are many analytical techniques for total arsenic, but very few that differentiate As(III) from As(V). Moreover, the Au(I) and other matrices interfere with quantitative analyses that are otherwise specific for As(III), while quantitative analyses for As that are not effected by Au(I) do not differentiate between As(III) and As(V). Thus a clear need exists for an analytic method for the quantitative determination of As(III) in the presence of As(V), Au(I) and Au(III).

OBJECTS OF THE INVENTION

It is a primary object of the invention to provide an analytic method for the quantitative determination of As(III) in the presence of As(V), Au(I), and Au(III).

It is thus an object of the invention to provide a quantitative analytical method for determining the concentration of As(III) in an Au(I) and Au(III)-containing electroplating solution, especially where the presence of Au(I) and Au(III) interferes with the quantitative determination of As(III).

SUMMARY OF THE INVENTION

These and other objects are achieved by the method of our invention. According to our invention there is provided a method of analyzing for As(III) as $AsO_2^{-1}$ ion in an Au(I) containing electroplating solution. The concentration of As(III) in the electroplating solution is maintained high enough to avoid formation of "burnt Au" but low enough to avoid wire bond failures. A sample of the electroplating solution is withdrawn and added to a buffered solution, for example an acetate-ethylene diamine tetraacetic acid (EDTA) buffered solution. A complexing agent for Au(I) ion is added to the buffered solution. This can be an alkali metal cyanide. Next ammonium pyrrolidine dithiocarbamate is added as a complexing agent for the $AsO_2^{-1}$ ion. The ammonium pyrrolidine dithiocarbamate—$AsO_2^{-1}$ ion is extracted, for example with methyl isobutyl ketone (MIBK). The extract is analyzed for As by electrothermal atomic absorption spectrometry.

DETAILED DESCRIPTION OF THE INVENTION

According to our invention there is provided a method of analyzing for As(III) as $AsO_2^{-1}$ ion in an Au(I) containing electroplating solution. The concentration of As(III) in the electroplating solution is maintained high enough to avoid formation of Au oxides but low enough to avoid bond failures. In an electroplating containing from about 3 grams per liter to about 30 grams per liter of KAu(CN)$_2$ this is generally from about 1 milligram per liter to about 15 milligrams per liter of an alkali metal arsenite, as NaAsO$_2$.

A sample of the electroplating solution is withdrawn and added to a buffered solution, for example an acetate-ethylene diamine tetraacetic acid (EDTA) buffered solution. Other buffering agents that may be used include phthalates, succinates, citrates, and maleates. The amount of buffering agent that is added is sufficient to keep the pH of the solution between about pH=5 and pH=6.

A complexing agent for Au(I) ion is added to the buffered solution. This can be an alkali metal cyanide. Typical alkali metals are Li, Na, K, Cs, and Rb, with NaCN and KCN preferred. The amount of complexing agent is determined by the amount of Au(I) in the electroplating solution, and is generally from about 100 to about 500 microliters per liter of a solution 2.5 grams of complexing agent per 100 ml.

Next, ammonium pyrrolidine dithiocarbamate is added as a complexing agent for the $AsO_2^{-1}$ ion. The amount of ammonium pyrrolidine dithiocarbamate is dependent on the concentration of $AsO_2^{-1}$ ion, and is generally from about 5 to about 100 milligrams per 25 cc.

The ammonium pyrrolidine dithiocarbamate—$AsO_2^{-1}$ ion is extracted, for example with methyl isobutyl ketone (MIBK). Other solvents that may be used include carbon tetrachloride and nitrobenzene, among others.

The extract is analyzed for As(III) by atomic absorption, as electrothermal atomic absorption spectrometry.

The method of the invention is shown by the following example.

A series of tests were run to determine the accuracy and precision of the method of the invention.

One gram of J. T. Baker B337 solid ammonium pyrrolidine dithiocarbamate (APDC) was dissolved in 100 milliliters of deionized water to provide an aqueous solution of APDC.

A stock arsenic solution of 1 mg/ml was prepared by weighing 0.1734 grams of NaAsO$_2$ in deionized water and diluting to 100 milliliters. A dilute arsenic solution was prepared by weighing 199 grams of deionized water into a 250 milliliter polyethylene bottle, and pipeting 1 milliliter of the stock arsenic solution into the bottle.

A spiking solution was prepared by pipeting 9.75 milliliter of deionized water into a small bottle, and micropipeting 250 microliters of Engelhard E-3 Brightener Concentrate to the the deionized water. This resulted in a solution containing 0.25 grams per liter of As(III).

A spiked sample was prepared by pipeting 10 milliliter of sample into a 50 milliliter polyethylene bottle, and pipeting 100 microliters of Engelhard E-3 Brightener dilute spiking solution into the bottle and mixing. This spiked solution had an As(III) spike of 2.5 milligrams per liter of As(III).

A buffer solution was prepared to buffer the solution under analysis to pH 5.0 to 6.0. A solution of 1 molar sodium acetate was prepared by diluting 138.1 grams of sodium acetate, $Na(CH_3COO) \times 3H_2O$, to one liter with distilled water. A solution of 1 molar acetic acid was prepared by diluting 57 milliliters of acetic acid, $CH_3COOH$, to 1 liter with deionized water. One molar acetic acid was added to sodium acetate solution until pH=5.2 was attained.

A 2.5 weight/volume percent sodium cyanide solution was prepared by weighing out 2.5 grams of NaCN and diluting with deionized water to 100 milliliters.

A 5 weight/volume percent solution of sodium ethylene diamine tetraacetate was prepared by weighing 50 grams of $Na_2EDTA \times 2H_2O$ into deionized water and diluting to 1 liter. An EDTA-buffer solution was then prepared by mixing 250 milliliters of the pH=5.2 sodium acetate-acetic acid solution and 250 milliliters of the 5 weight/volume percent EDTA solution.

A matrix solution was prepared by dissolving 103 grams of Engelhard Conducting salts C, an approximately equal parts by weight solid mixture of citrates and pyrophosphates, in 400 ml of deionized water. To this solution was added 9.8 grams of Engelhard E75 Gold Salts, solid $KAu(CN)_2$. The pH of the solution was adjusted to pH=5.9 by the addition of Engelhard Acid B, solid citric acid.

For the analytical tests a Perkin Elmer Model 5100 Zeeman Graphite Furnace Atomic Absorption device was used. It had a wavelength of 193.7 nanometers, a slit 0.7 low, a read time of 5 seconds, a read delay of 0, a BOG time of 2 seconds. The furnace was operated according to the following time temperature program:

| Step | Temp (deg C.) | Ramp (sec) | Hold (sec) | Gas Flow (ml per min) | Read | Gas Type |
|---|---|---|---|---|---|---|
| 1 | 70 | 1 | 20 | 300 | | Norm |
| 2 | 130 | 1 | 30 | 300 | | Norm |
| 3 | 200 | 5 | 15 | 300 | | Norm |
| 4 | 20 | 1 | 10 | 300 | | Norm |
| 5 | 2100 | 0 | 5 | 0 | * | Norm |
| 6 | 2600 | 1 | 5 | 300 | | Norm |

In carrying out the tests a series of laboratory standards were first prepared. These were prpeared by adding 13 ml of deionized water to each of three 60 milliliter separatory funnels. Ten milliliters of the EDTA/buffer solution was pipeted into each separatory funnel. Next 100 microliters of the matrix solution was pipeted into each of the separatory funnels. Then 0, 50, and 100 microliters of the dilute arsenic solution were pipeted into each separatory funnel respectively. These standards, as prepared, were respectively equal to 0, 25, and 50 micrograms per liter As(III). These standard samples were then analyzed as follows.

Samples for analysis were prepared by adding 13 milliliters of deionized water to a 60 milliliter separatory funnel, pipeting 10.0 milliliters of the EDTA/buffer solution into the funnel, pipeting 100 microliters of the sample to be tested into the separatory funnel, and mixing.

The above steps, for both the sample and the standards, were followed by pipeting 200 microliters of the 2.5 weight/volume percent sodium cyanide solution into the solution to be tested, mixing, adding 2.0 milliliters of APDC and mixing, and then pipeting 10.0 milliliters of methyl isobutyl ketone solvent, shaking vigorously for thirty seconds, and letting stand for one minute. The bottom or water layer was discarded. The organic phase was recovered and poured into a graphite furnace atomic absorption sample cup. The sample was then tested according to the above time-tmperature profile.

The As(III) was calculated according to the following equation:

$$As(III) \; mg/l = microgram/l \; from \; GFAA \times 0.1$$

Accuracies within ±10 percent, comparing as prepared to analysis, were obtained.

Thus, according to the invention there is provided an analytic method for the quantitative determination of As(III) in the presence of both As(V), Au(I) and Au(III). This analytic method allows determining the concentration of As(III) in an Au(I) and Au(III) containing electroplating solution, especially where the presence of Au(I) interferes with the quantitative determination of As(III), as well as determining the concentration of As(III) in the presence of As(V), as is the case in an Au(I)-containing electroplating solution, especially where the presence of either or both of Au(I) and As(V) interfere with the quantitative determination of As(III).

While the invention has been described with respect to certain preferred embodiments and exemplifications, it is not intended to limit the scope of the invention thereby, but solely by the claims appended hereto.

We claim:

1. A method of analyzing for As(III) as $AsO_2^{-1}$ ion in an Au(I) and Au(III) containing electroplating solution, said method comprising the steps of:

a. adding a sample of the electroplating solution to a buffered solution;

b. adding a complexing agent for Au(I) ion to the buffered solution, wherein the complexing agent for Au(I) is an alkali metal cyanide having the formula MCN where M is an alkali metal chosen from the group consisting of Li, Na, K, Rb, and Cs;

c. adding ammonium pyrrolidine dithiocarbamate as a complexing agent for the $AsO_2^{-1}$ ion;

d. extracting the ammonium pyrrolidine dithiocarbamate—$AsO_2^{-1}$ ion; and e. analyzing the extracted ammonium pyrrolidine dithiocarbamate—$AsO_2^{-1}$ ion for As.

2. The method of claim 1 wherein the alkali metal is Na.

3. The method of claim 1 wherein the alkali metal is K.

4. The method of claim 1 wherein the buffered solution comprises an aqueous acetate—ethylene diamine tetraacetic acid solution.

5. The method of claim 1 comprising extracting the ammonium pyrrolidine dithiocarbamate—$AsO_2^{-1}$ ion with methyl isobutyl ketone.

6. The method of claim 1 comprising analyzing the extracted ammonium pyrrolidine dithiocarbamate—$AsO_2^{-1}$ ion for As by atomic absorption spectrometry.

7. The method of claim 6 comprising analyzing the extracted ammonium pyrrolidine dithiocarbamate—$AsO_2^{-1}$ ion for As by electrothermal atomic absorption spectrometry.

8. A method of electroplating Au(I) from an As(III) containing electroplating solution onto a substrate, wherein the concetration of As(III) in the electroplating solution is maintained high enough to avoid formation of burnt deposits but low enough to avoid bond failures, comprising establishing an electrical potential between an anode and a substrate to be electroplated, and electroplating Au thereon, the further steps comprising:

a. adding electroplating solution to a buffered solution;

b. adding a complexing agent for Au(I) ion to the buffered solution, wherein the complexing agent for Au(I) ion is an alkali metal cyanide having the formula MCN where M is an alkali metal chosen from the group consisting of Li, Na, K, Rb, and Cs;

c. adding ammonium pyrrolidine dithiocarbamate as a complexing agent for $AsO_2^{-1}$ ion;

d. extracting the ammonium pyrrolidine dithiocarbamate—$AsO_2^{-1}$ ion;

e. analyzing the extracted ammonium pyrrolidine dithiocarbamate—$AsO_2^{-1}$ ion for As; and f. thereafter adjusting the concentration of gold and As in in the electroplating solution in response to the $AsO_2^{-1}$ concentration.

9. The method of claim 8 where the alkali metal is Na.

10. The method of claim 8 where the alkali metal is K.

11. The method of claim 8 wherein the buffered solution comprises an aqueous acetate—ethylene diamine tetraacetic acid solution.

12. The method of claim 8 comprising extracting the ammonium pyrrolidine dithiocarbamate—$AsO_2^{-1}$ ion with methyl isobutyl ketone.

13. The method of claim 8 comprising analyzing the extracted ammonium pyrrolidine dithiocarbamate—$AsO_2^{-1}$ ion for As by atomic absorption spectrometry.

14. The method of claim 13 comprising analyzing the extracted ammonium pyrrolidine dithiocarbamate—$AsO_2^{-1}$ ion for As by electrothermal atomic absorption spectrometry.

* * * * *